US012805775B2

(12) United States Patent
Zhu et al.

(10) Patent No.: US 12,805,775 B2
(45) Date of Patent: Nov. 24, 2026

(54) DETERMINING OXYGEN LEVELS FROM IMAGES OF SKIN

(71) Applicant: Samsung Electronics Co., Ltd., Suwon-si (KR)

(72) Inventors: Li Zhu, Saratoga, CA (US); Korosh Vatanparvar, San Jose, CA (US); Michael Chan, Atlanta, GA (US); Migyeong Gwak, Santa Clara, CA (US); Jungmok Bae, Menlo Park, CA (US); Jilong Kuang, San Jose, CA (US); Jun Gao, Menlo Park, CA (US)

(73) Assignee: Samsung Electronics Co., Ltd., Suwon-si (KR)

( * ) Notice: Subject to any disclaimer, the term of this patent is extended or adjusted under 35 U.S.C. 154(b) by 718 days.

(21) Appl. No.: 18/213,461

(22) Filed: Jun. 23, 2023

(65) Prior Publication Data

US 2024/0016424 A1 Jan. 18, 2024

Related U.S. Application Data

(60) Provisional application No. 63/443,944, filed on Feb. 7, 2023, provisional application No. 63/389,771, filed on Jul. 15, 2022.

(51) Int. Cl.
*A61B 5/1455* (2006.01)

(52) U.S. Cl.
CPC ................................ *A61B 5/14552* (2013.01)

(58) Field of Classification Search
CPC .................................................... A61B 5/1455
See application file for complete search history.

(56) References Cited

U.S. PATENT DOCUMENTS

| | | | |
|---|---|---|---|
| 10,521,900 | B2 | 12/2019 | Bartula |
| 11,020,030 | B2 | 6/2021 | Tao |
| 11,229,372 | B2 | 1/2022 | Tao |
| 11,324,406 | B1 | 5/2022 | Nour |
| 11,432,727 | B2 | 9/2022 | Han |

(Continued)

FOREIGN PATENT DOCUMENTS

| | | | |
|---|---|---|---|
| CN | 112869737 | A | 6/2021 |
| CN | 113397535 | A | 9/2021 |

(Continued)

OTHER PUBLICATIONS

Non-contact measurement of oxygen saturation with an RGB camera. Biomedical Optics Express, Aug. 11, 2015 (Year: 2015).*

(Continued)

*Primary Examiner* — Marjan Fardanesh

(57) ABSTRACT

In one embodiment, a method includes accessing a sequence of images of a portion of a person's skin illuminated by ambient light and determining, from at least one of the images, a plurality of microregions in the portion of the person's skin. The method further includes determining, based on a similarity between particular microregions of the plurality of microregions, one or more regions of interest of the person's skin; determining, for each of the regions of interest, a remote photoplethysmogram (rPPG) signal based on the sequence of images; and determining, based on one or more of the rPPG signals, an estimate of an oxygen saturation in the person's blood.

20 Claims, 10 Drawing Sheets

(56) References Cited

U.S. PATENT DOCUMENTS

| | | | | |
|---|---|---|---|---|
| 2007/0024946 | A1* | 2/2007 | Panasyuk ............... | A61B 5/416 359/253 |
| 2016/0113531 | A1 | 4/2016 | Visvanathan | |
| 2017/0238805 | A1 | 8/2017 | Addison | |
| 2018/0153455 | A1 | 6/2018 | Guazzi | |
| 2021/0015376 | A1 | 1/2021 | Kim | |
| 2021/0153752 | A1 | 5/2021 | Park | |
| 2022/0409078 | A1 | 12/2022 | Sperrhake | |
| 2023/0000377 | A1 | 1/2023 | Wu | |
| 2023/0091866 | A1 | 3/2023 | White | |
| 2024/0016424 | A1 | 1/2024 | Zhu | |

FOREIGN PATENT DOCUMENTS

| | | | |
|---|---|---|---|
| CN | 114758400 | A | 7/2022 |
| EP | 3 838 128 | A1 | 6/2021 |
| EP | 4076186 | | 6/2021 |
| JP | 2018-038553 | | 3/2018 |
| JP | 2021-153878 | | 10/2021 |
| KR | 10-2015-0095661 | | 8/2015 |
| KR | 10-2411622 | B1 | 6/2022 |
| WO | WO 2023-091576 | A1 | 5/2023 |

OTHER PUBLICATIONS

PCT International Search Report in Application No. PCT/KR2023/009997, Oct. 26, 2023.

PCT Written Opinion of the International Searching Authority in Application No. PCT/KR2023/009997, Oct. 26, 2023.

"Noncontact Monitoring of Blood Oxygen Saturation Using Camera and Dual-Wavelength Imaging System" Shao et al., IEEE Transactions on Biomedical Engineering, vol. 63, No. 6, Jun. 2016.

PCT International Search Report and Written Opinion in Application No. PCT/KR2024/012340, Nov. 22, 2024.

Extended European Search Report in Application No. 23839982.8-1113 / 4518755 PCT/KR2023009997, Mar. 18, 2025.

Notice of Allowance in U.S. Appl. No. 18/759,674, Apr. 17, 2026.

Petersen et al. "Remote Estimation of Peripheral Oxygen Saturation and Pulse Rate from Facial Analysis Using a Smartphone Camera" 45th Annual International Conference of the IEEE Engineering in Medicine and Biology Society (EMBC), Sydney, Australia, 2023, pp. 1-4, doi: 10.1109/EMBC40787.2023.10340995, Jul. 1, 2023.

Extended European Search Report in Application No. 24863072.5-113 / 4673048 PCT/KR2024012340, Mar. 11, 2026.

Chan, Michael et al. "Estimating SpO2 with Deep Oxygen Desaturations from Facial Video Under Various Lighting Conditions: A Feasibility Study"; 2023 45th Annual International Conference of the IEEE Engineering in Medicine & Biology Society , IEEE, Jul. 24, 2023, pp. 1-5, Jul. 24, 2023.

Li, Zhu, et al: "Contactless SpO2 Detection from Face Using Consumer Camera"; 2022 IEEE-EMBS International Conference on Wearable and Implantable Body Sensor Networks (BSN), IEEE, pp. 1-4, Sep. 27, 2022.

Communication pursuant to Article 94(3) EPC in EPO Application No. 23 839 982.8-1113, Apr. 9, 2026.

* cited by examiner

DETERMINING OXYGEN LEVELS FROM IMAGES OF SKIN

PRIORITY CLAIM

This application claims the benefit under 35 U.S.C. § 119 of U.S. Provisional Patent Applications 63/389,771 (filed Jul. 15, 2022) and 63/443,944 (filed Feb. 7, 2023), each of which is incorporated by reference herein.

TECHNICAL FIELD

This application generally relates to determining oxygen levels from images of skin.

BACKGROUND

Changes in blood volume in the blood vessels of a human body relate to important physiological phenomena. For example, blood-volume pulses correspond to a person's heartbeat and blood pressure. In addition, changes in blood volume can be used to estimate oxygen levels in a person's blood. For example, changes in blood volume can provide information about oxygen saturation (SpO2), which is a measure of the percentage of oxygen-bounded hemoglobin over the total hemoglobin in a user's blood.

DESCRIPTION OF EXAMPLE EMBODIMENTS

The oxygen saturation of a person's blood (SpO2) can be measured using an arterial blood gas test. This test requires taking a blood draw from a person's artery and must be performed in a clinical setting. The test is invasive and painful, and is not continuous in that each blood draw only provides information about a person's SpO2 at the point in time corresponding to the blood draw. In addition, the arterial blood gas test does not provide immediate results because the drawn blood must be sent to a lab for analysis.

A finger pulse oximeter is a non-invasive test that uses light to estimate a person's SpO2. However, a finger pulse oximeter requires continuous contact with a person's finger, e.g., by being clamped to the finger, and therefore the test does not provide a convenient measurements of a person's SpO2—particularly continuous measurements, as those would require a person to leave the pulse oximeter attached to their finger over time, limiting use of that hand. In addition, because a finger pulse oximeter requires contact with a person's finger, this approach can spread infections when the same oximeter is used by different people.

Non-invasive SpO2 measurements that use light rely on a ratio-of-ratios technique to estimate SpO2 in a person's blood. When light from a light source is incident on a person's skin, some of the incident light reflects off the surface of a person's skin, known as specular reflection, and some of the light passes into the person's tissue. The person's tissue also reflects some light, and some of this reflected light may travel back through the person's tissue and pass out of the person's skin, known as diffuse reflection. A light sensor can capture both light from specular reflection and light from diffuse reflection. The characteristics of specular and diffuse reflection depend in-part on the wavelength of incident light. The ratio-of-ratios is derived based on the differential absorption of oxygenated hemoglobin (HbO2) and deoxygenated hemoglobin (HbR) at two or more different wavelengths, which correlates with blood oxygen saturation.

Figure 1:
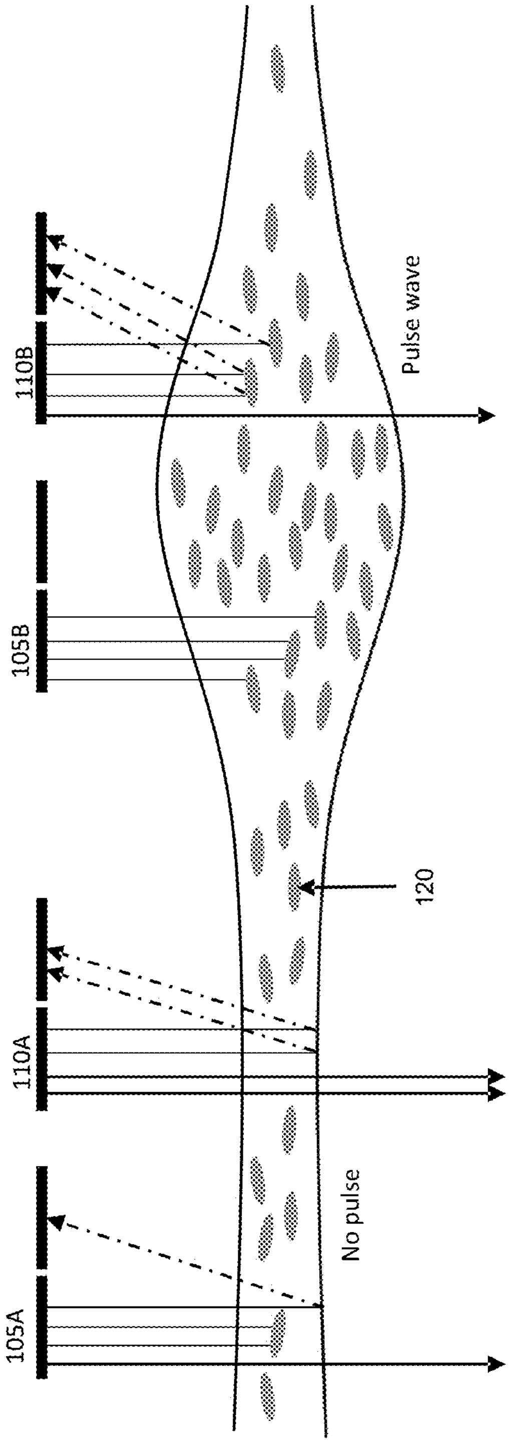
FIG. 1 illustrates an example of light interacting with blood in a person's artery.

Diffuse reflection can vary based on the amount of blood that the light interacts with. FIG. 1 illustrates a simplified example in which light 105A-B having a first wavelength (e.g., green light) and light 110A-B having a second wavelength (e.g., red light) interacts with blood in a person's artery. The blood contains several red blood cells 120. As illustrated in FIG. 1, when the blood is not subject to a pulse, then some light 105A is absorbed by red blood cells, some is reflected off the person's tissue, and some passes through the person's tissue. Some light 110A is reflected off the person's red blood cells and tissue, and some light 110A passes through the person's tissue. However, when the person's blood is subject to a pulse, the number of red blood cells 120 increases in a given arterial region, and as a result, light 105B is more likely to be absorbed by red blood cells 120 while light 110B is more likely to be reflected off of red blood cells 120. Thus, the relative reflectance of different wavelengths of light when the blood is static vs. pulsed indicates the presence of red blood cells, which correspond to blood-oxygen levels.

More formally, the light $R_c$, for a given wavelength c, reflected off a person's skin is represented by:

$$R_c = \sum_{\lambda_c} L\left(\lambda, \vec{x}, t\right) s\left(\lambda, \vec{x}, t\right) r_c(\lambda, t),$$

where $r_c(\lambda,t)$ represents the sensor response for a given wavelength c; $s(\lambda, \vec{x}, t)$ represents the light reflectance, which is equal to $=m(\lambda, \vec{x})b(\lambda, \vec{x}, t)$; and $L(\lambda, \vec{x}, t)$ represents the incident light, which is equal to $=l(\vec{x}, t)\hat{L}(\lambda)$. In these equations, $m(\lambda, \vec{x})$ corresponds to specular reflection, which represents the effect from non-blood tissue (e.g., melanin, water, etc.). $b(\lambda, \vec{x}, t)$ corresponds to diffuse reflect, which represents the effect from blood-light interactions. $\hat{L}(\lambda)$ represents the spectral distribution of the incident light and t) represents the intensity of the incident light. The time-dependent diffuse reflection can be represented as:

$$b\left(\lambda, \vec{x}, t\right) = v\left(\vec{x}, t\right) b_{DC}(\lambda, t) + \Delta v\left(\vec{x}, t\right) b_{AC}(\lambda, t),$$

where v represents the volume of static (no-pulse) blood, $\Delta v$ represents the volume of pulsatile blood; $b_{DC}(\lambda,t)$ represents the reflectance of static blood; and $b_{AC}(\lambda,t)$ represents the reflectance of pulsatile blood.

In the ratio-of-ratio technique, the effect of light intensity can be removed from the light response by:

$$\hat{R}_c(t)=\frac{I(\vec{x},t)\sum_{\lambda_c}\hat{L}(\lambda)r_c(\lambda)m(\lambda,\vec{x})\Delta v(\vec{x},t)b_{AC}(\lambda,t)}{I(\vec{x},t)\sum_{\lambda_c}\hat{L}(\lambda)r_c(\lambda)m(\lambda,\vec{x})v(\vec{x},t)b_{DC}(\lambda,t)},$$

which can be rewritten as:

$$\hat{R}_c(t)=\frac{\Delta v(\vec{x},t)}{v(\vec{x},t)}\frac{\sum_{\lambda_c}\hat{L}(\lambda)r_c(\lambda)m(\lambda,\vec{x})b_{AC}(\lambda,t)}{\sum_{\lambda_c}\hat{L}(\lambda)r_c(\lambda)m(\lambda,\vec{x})b_{DC}(\lambda,t)},$$

The dependency on blood volume can be eliminated by:

$$S(t)=\frac{\sum_{\lambda_1}\hat{L}(\lambda)r_c(\lambda)m(\lambda,\vec{x})b_{AC}(\lambda,t)\sum_{\lambda_2}\hat{L}(\lambda)r_c(\lambda)m(\lambda,\vec{x})b_{DC}(\lambda,t)}{\sum_{\lambda_1}\hat{L}(\lambda)r_c(\lambda)m(\lambda,\vec{x})b_{DC}(\lambda,t)\sum_{\lambda_2}\hat{L}(\lambda)r_c(\lambda)m(\lambda,\vec{x})b_{AC}(\lambda,t)}$$

which can be rewritten as:

$$S(t)=\frac{AC_1/DC_1}{AC_2/DC_2},$$

where AC and DC refer to the pulsatile elements and non-pulsatile elements of the signal, at their respective subscripted wavelengths. As discussed more fully herein, S(t) is only related to blood reflectance if specular reflection is spatially invariant across the measured sample, i.e., if $m(\lambda,\vec{x})=m(\lambda)$.

For the ratio-of-ratios technique to accurately reflect SpO2, the specular reflectance of the skin must be uniform in the measurement area. For remote PPG sensing, which attempts to measure SpO2 using non-contact light-sensing techniques, this uniformity requirement presents a significant challenge due to the non-uniformity of the human skin and due to user movement during measurement time. For example, a portion of a person's skin, such as the person's face, can have spatially varying reflectance properties due to variations in skin tissues (e.g., the presence of hair, color and thickness variations in the user's skin, moles, etc.). In addition, while movement is a non-issue in finger pulse oximetry due to the sensor being clamped to a specific portion of the user's finger, in remote PPG the person can move relative to the measurement apparatus (e.g., a camera), and this relative movement can affect the measurement results.

Figure 2:
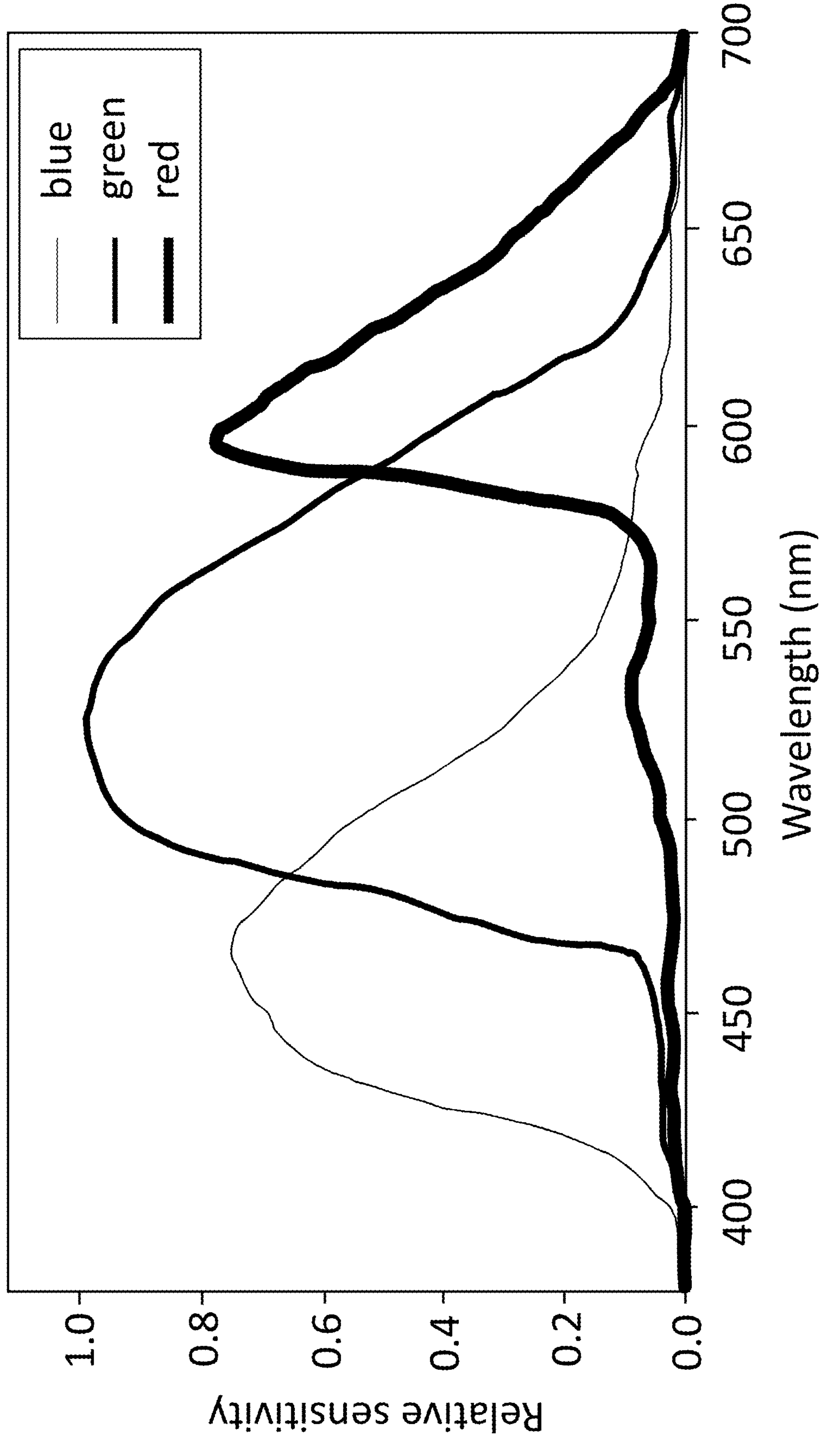
FIG. 2 illustrates an example response of an example smartphone camera's red, green, and blue sensors.

In addition, the ratio-of-ratios technique assumes that a sensor (e.g., camera) can independently detect two different wavelengths of light. For example, a finger pulse oximeter uses specialized sensors that detect red light and IR light, respectively, and the sensitive ranges of these sensors do not overlap. However, consumer cameras do not meet this requirement, as the camera response in different color channels (e.g., different wavelengths or ranges of wavelengths) overlaps between channels. For example, FIG. 2 illustrates an example response of an example smartphone camera's red, green, and blue sensors. As illustrated in FIG. 2, the camera sensor response in the blue channel overlaps with the sensor response in the green channel, etc., and an rPPG signal associated with this wide-band spectra creates complicated nonlinearity for SpO2 mappings, making the ratio-of-ratio technique unsuitable for estimating SpO2.

Figure 3:
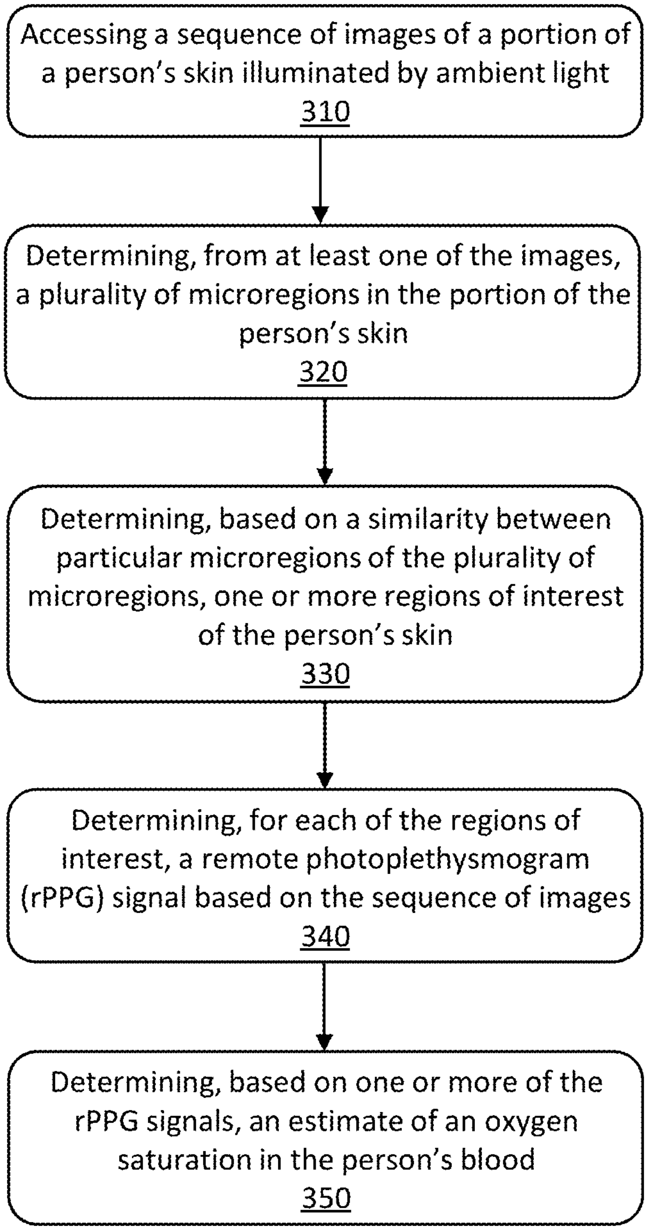
FIG. 3 illustrates an example method for using an RGB camera to measure a person's SpO2 under ambient lighting conditions.

FIG. 3 illustrates an example method for using an RGB camera to accurately and remotely measure a person's SpO2 under ambient lighting conditions. Step 310 of the example method of FIG. 3 includes accessing a sequence of images of a portion of a person's skin illuminated by ambient light. The ambient light can include natural light; lighting from lamps, luminaires, and other light fixtures; and light from electronic devices such as a display screen in a smartphone, monitor, TV, etc. The images are captured by any suitable camera, such as the front or back camera of a smartphone, a web camera, a TV or laptop camera, a consumer camera device, etc. In particular embodiments, the accessing step of 310 includes capturing the images of the portion of the person's skin, for example by one or more of the camera devices described above. In step 310, the images may be accessed from any suitable device, such as a camera device, a device that includes a camera (e.g., a smartphone), a server device, etc. In particular embodiments, step 310 may be performed at or near the same time the images are captured. In particular embodiments, step 310 may be performed at some time after such images are captured, in which case the resulting SpO2 estimate corresponds to the time that the images were captured. The sequence of images are captured contemporaneously, and in particular embodiments, the sequence of images may be images consecutively captured by the camera(s).

Figure 4:
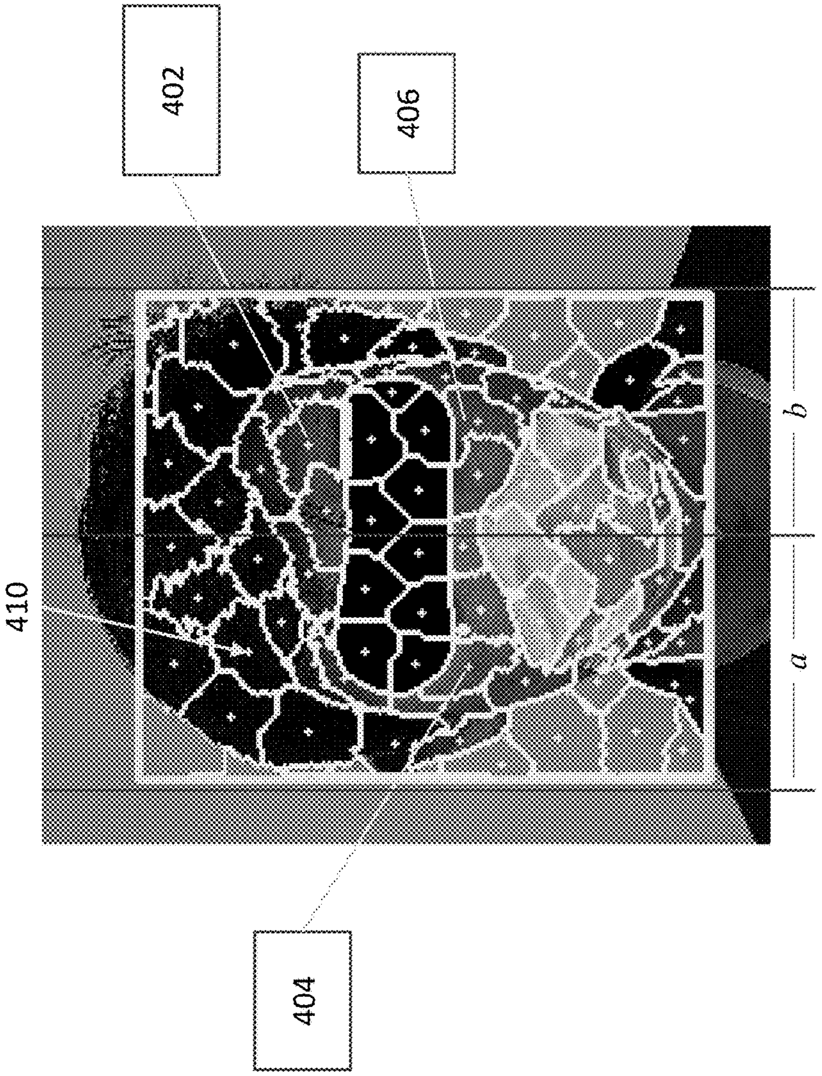
FIG. 4 illustrates an example of a human face divided into a number of microregions.

Step 320 of the example method of FIG. 3 includes determining, from at least one of the images, a plurality of microregions in the portion of the person's skin. The microregions each identify a subset of the portion of the person's skin. FIG. 4 illustrates an example of a human face divided into a number of microregions including microregions 402, 404, and 406. Each microregion has a center, e.g., 410. For example, the portion of the person's skin may be the face, and the step 320 then includes subdividing the image of the face into a number of microregions. Before creating microregions, particular embodiments may use object detection, such as face detection, to detect and delineate the portion of the person's skin. For example, the images may be processed by a facial-recognition algorithm to determine the rough location of the portion of the person's skin (e.g., the face). In particular embodiments, the portion of the person's skin may be predetermined beforehand (e.g., an embodiment may perform the example method of FIG. 3 specifically on the face or hand, etc.), and the images may be sent to a classifier to determine whether the specific portion is present in the sequence of images.

Particular embodiments may determine microregions according to the techniques described in Patent Application Publication No. 2023/0128766 which is incorporated herein by reference. However, this disclosure contemplates that any suitable technique for determining microregions of a portion of human skin may be used in step 320. Once determined, whether from one image or from multiple images, the mROIs are tracked (i.e., associated with their respective skin regions) across all of the input images.

Step 330 of the example method of FIG. 3 includes determining, based on a similarity between particular microregions of the plurality of microregions, one or more regions of interest of the person's skin. The similarity between two microregions (mROIs) may be based on the similarity between skin properties $S_i$ corresponding to the respective two microregions, such as skin tone, thickness, etc. As explained more fully herein, if the skin properties of two or more microregions are sufficiently similar, then those microregions may be combined into a larger region of interest (ROI). Thus, this process overcomes the challenges due to the spatially varying, non-uniform reflection properties of human skin.

Figure 5:
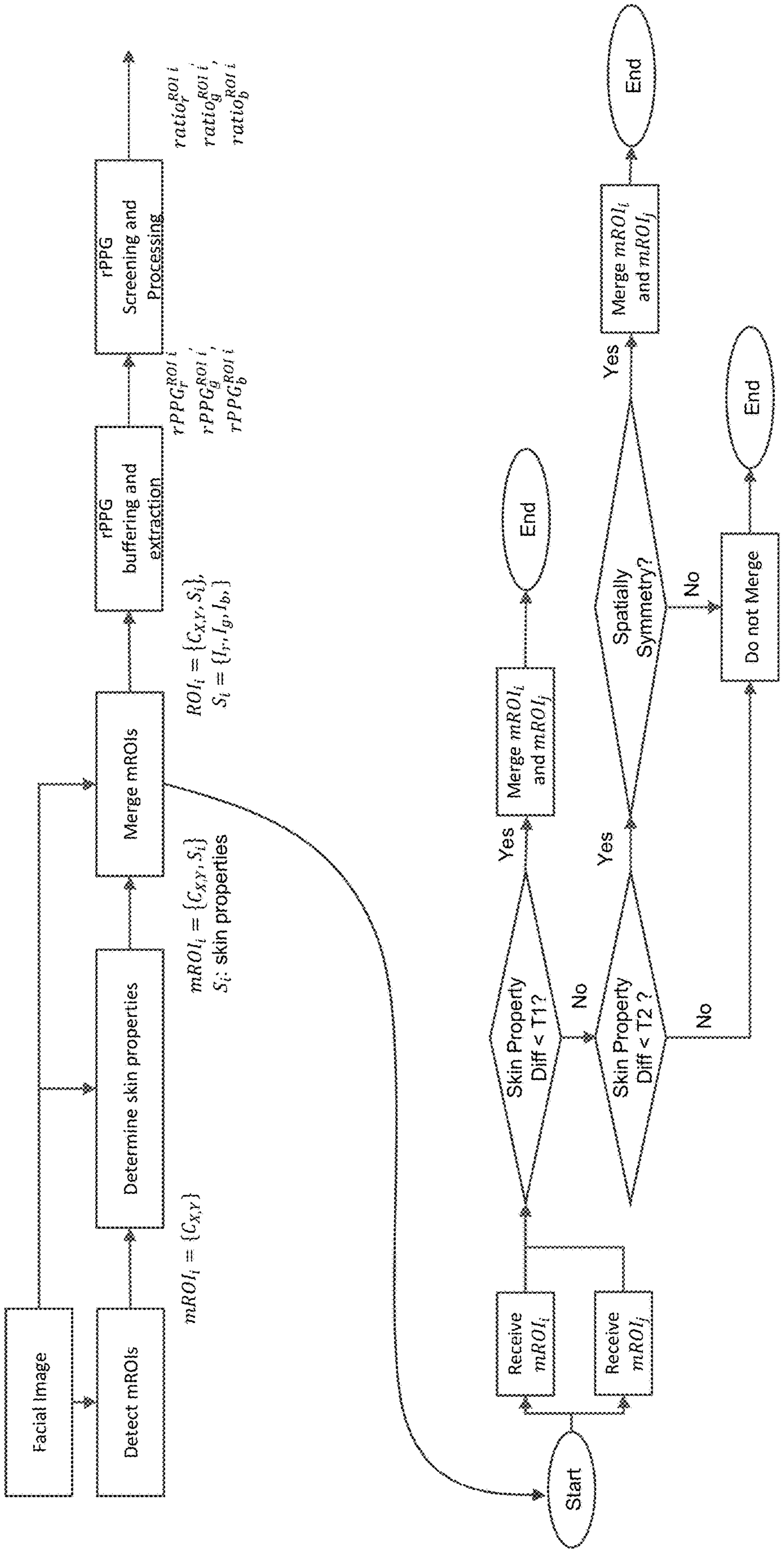
FIG. 5 illustrates an example process for merging mROIs to ROIs.

FIG. 5 illustrates an example process for merging mROIs to ROIs using a facial image. In the example of FIG. 5, after the facial image is divided into a number of microregions (e.g., as in the example of FIG. 4), then skin properties of each mROI are determined. The merger process may be performed for each pair of mROIs determined in step 320. As a result, more than two mROIs may be merged into a single ROI. In particular embodiments, some mROIs may not be merged with any other mROIs (i.e., they may form an ROI by themselves).

Each microregion is defined by its boundaries $C_{X,Y}$, which identifies all the X,Y coordinates of all pixels within that mROI. In particular embodiments, the skin properties of an mROI may be determined based on the pixel values of the pixels within that mROI. For example, the skin properties of an mROI may be determined based on the average intensity of all pixels within the mROI for a given color channel (e.g., red, green, blue), resulting in channel-specific intensities $I_r$, $I_y$, $I_b$ for each mROI. While this example refers to the RGB color channels, this disclosure contemplates that other color-channel representations may be used.

In the example of FIG. 5, the determined skin properties, along with the boundary location information $C_{X,Y}$, for each mROI are sent to an mROI merger block, which determines whether to combine mROIs based on combination criteria. For example, the combination criteria may be performed based on comparing the similarities of the averaged color intensities based on $I_r$,$I_g$,$I_b$, and on the location symmetry based on $C_{X,Y}$ between mROIs. FIG. 5 illustrates an example process for determining whether to merge two mROIs i and j. In the example of FIG. 5, the skin properties (e.g., the average intensity of pixel values for each color channel) of $mROI_i$ and $mROI_j$ are compared to determine the difference between the skin properties for those two mROIs. If the difference is less than a first threshold $T_1$, then the two mROIs may be merged into an ROI. In particular embodiments, if the difference is not less than $T_1$, then the mROIs may be still be merged if both of: (1) the difference in skin properties is less than a second threshold $T_2$, where $T_2$ is less demanding than $T_1$, and (2) the two mROIs exhibit spatial symmetry. For example, mROIs 404 and 406 in FIG. 4 are spatially symmetric, and therefore those mROIs may be merged if the differences in skin properties satisfies the threshold $T_2$ but fails the threshold $T_1$. Thus, as illustrated in this example, non-contiguous mROIs may be merged into an ROI. In particular embodiments, $T_1$ may be 0.95 and $T_2$ may be 0.9.

Notably, this example process increases the number of pixels in each ROI (by merging similar mROIs) while maintaining the skin-homogeneity assumptions necessary to accurately determe SpO2 using the ration-of-ratios technique. The signal-to-noise (SNR) ratio in the PPG signal is proportional to the number of pixels in the ROI, and therefore more pixels is better for ensuring quality signals. However, pixels that violate the skin-homogeneity assumptions necessary for the ratio-of-ratios technique should not be included in the same ROI, and therefore the example process described above improves SNR by increasing the number of pixels in each ROI while ensuring that the skin-homogeneity assumption still apply.

In particular embodiments, the value of thresholds $T_1$ and $T_2$ can be customized based on the person's skin tone and/or on the ambient light intensity, as explained herein. In particular embodiments, the value of thresholds $T_1$ and $T_2$ can compensate for uneven light incident on the portion of the person's skin, e.g., between one side of the face and the other side of the face. For example, if the light source in the example of FIG. 4 comes from the person's right-hand side, the light reflection will be stronger in mROI 404 compared to mROI 406, which may result in artifact skin-property differences between these two microregions even if the skin properties are the same. To correct these artifacts, particular embodiments may introduce a coefficient $C_i$ that is used to multiply each micro-ROI $mROI_i$, where i represents the index of the micro-ROI. In one embodiment, the coefficients are negatively correlated to the averaged light intensity of all skin pixels in a particular section of the image. For instance, in the example of FIG. 4, the coefficients may negatively correlated to the averaged light intensity of all skin pixels in columns a and b, respectively. If the averaged light intensity of skin pixels in column b is larger than the average intensity of skin pixels in column a, then $C_i$ should be smaller for micoregions in column b than for micoregions in column a in order to compensate the uneven light intensity incident on those different skin region.

Step 340 of the example method of FIG. 3 includes determining, for each of the regions of interest, a remote photoplethysmogram (rPPG) signal based on the plurality of images. For instance, in the example of FIG. 5, the output of the merge mROIs block includes the boundaries of each identified ROI and the skin properties (e.g., the average pixel intensity, per color channel) for that ROI. These outputs are buffered and raw rPPG signals are created, for each color channel and for each ROI, by concatenating the intensities within a time period t (i.e., using the sequence of images corresponding to the time period t). For example, once an ROI i is determined from an image, then that ROI may be tracked across the sequence of images, and three rPPG signals are generated for that ROI i: one in the red channel $$\left(\text{i.e., } rPPG_r^{ROI\,i}\right),$$

one in the blue channel, and one in the green channel.

Figure 6:
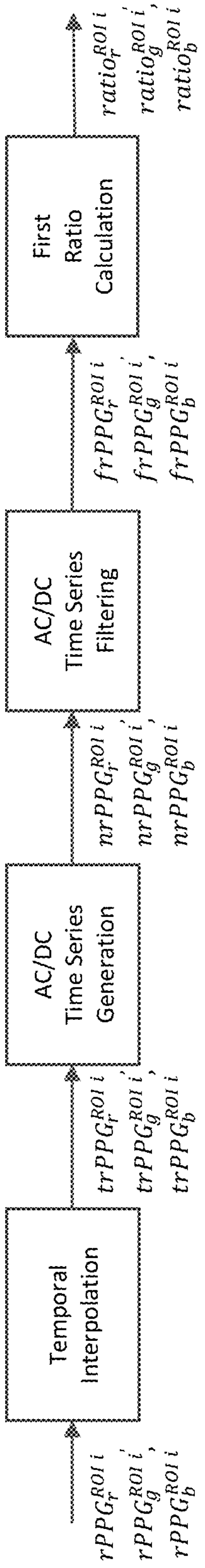
FIG. 6 illustrates an example process of an rPPG screening and processing block.

In the example of FIG. 5, the output of the rPPG buffering and extraction process is sent to an rPPG screening and processing block. This block generates "first ratio" values in the ratio-of-ratios framework for each color channel for each ROI $$\left(\text{e.g., a } \text{ratio}_r^{ROI\,i}\right.$$

corresponding to the red channel of the ith ROI). FIG. 6 illustrates an example process of this block. As shown in FIG. 6, the input is the three rPPG signals generated for each ROI. The example of FIG. 6 uses temporal interpolation to compensate uneven sampling intervals caused by the sensor (e.g., camera). The result is provided to an AC/DC time series generation block. For example, this block may normalize each $$trPPG_n^{ROI\ i}$$

signals by its respective DC component. The DC component may be computed by averaging all sample points within the given time window t. The obtained normalized time series nrPPG (one for each color channel) are then sent to the AC/DC time series filtering block to retain only cardiovascular-related components and remove higher frequency components (e.g., caused by motion or muscle activity) and lower frequency components (e.g., baseline drift or respiration-related wandering). The filtered AC/DC time series are then used to make first ratio calculations, again for each color channel for each ROI. In particular embodiments, the first ratio can be quantified by the average envelop amplitude of the AC/DC time series. In other embodiments, the first ratio can be quantified by first identifying the heartbeat-related peaks and troughs on the AC/DC time series, and then using the peak-to-trough amplitude as the proxy of the first ratio. In particular embodiments, as in the example of FIG. 6, the AC-over-DC components are derived from individual ROIs, and as a result the specular reflection components can be canceled out because the homogeneous skin-property assumption has been met.

Step 350 of the example method of FIG. 3 includes determining, based on one or more of the rPPG signals, an estimation of an oxygen saturation in the person's blood. In particular embodiments, normalized rPPG signals for different ROIs may be merged into rPPG signals, for a particular color channel. SpO2 from different portions of a person's skin (e.g., different portions of the face) are not similarly distributed. As a result, different parts of, e.g., a person's face can have different SpO2 values at a particular point in time. For example, SpO2 at the forehead may be slightly higher than at the cheek. Particular embodiments use pulse transit time (PTT) to select and/or weight ROIs in order to use those ROIs that exhibit similarly distributed SpO2 values. For instance, delta pulse transit time between two ROIs can be used as a metric to assess how closely related two ROIs are. Here, delta PTT is defined as the delay between PPG signals from different ROIs. The delay can be computed as the time required to shift one signal such that its normalized cross correlation with the other signal is maximized. For example, a delay τ between a first PPG signal $S_1$ from a first ROI and a second PPG sigal $S_2$ from a second ROI can be estimated according to:

$$\mathrm{Corr}(\tau) = \sum_{t=0}^{N-1} s_1(t)s_2(t+\tau)$$

$$\tau_{estimated} = \arg\max_{\tau}(\mathrm{Corr}(\tau))$$

Figure 7:
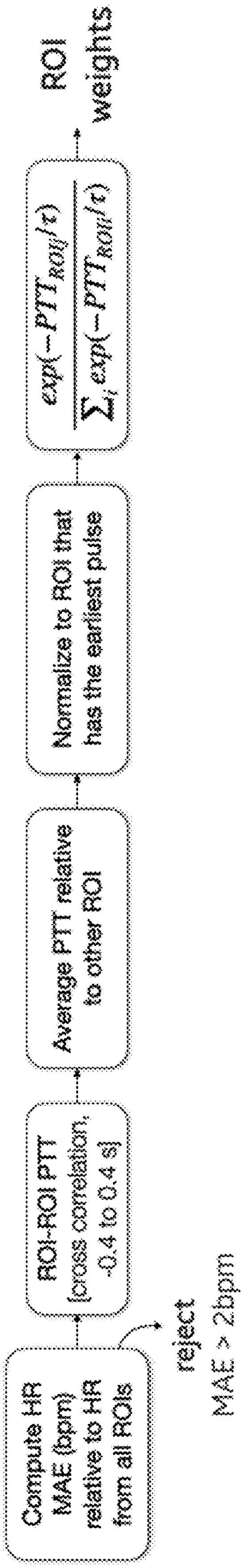
FIG. 7 illustrates an example approach for generating weights for rPPG signals from corresponding ROIs.

This estimated value of τ can then be used to generate weights for the rPPG signals for each ROI. For instance, FIG. 7 illustrates an example approach for generating weights for different rPPG signals from different ROIs. For a given color channel, the rPPG signals corresponding to the ROIs can then be interpolated using a weighted average to generate a final rPPG signal for that color channel.

Particular embodiments may use an adaptive SpO2 estimation process to assess the lighting environment at the time the images were taken to determine the color pairs (i.e., the pair of color channels) used for SpO2 estimation. Then, the rPPG signals for these color channels are used to determine the second ratio within the ratio-of-ratios framework. Particular embodiments use a non-linear machine learning model, trained to estimate SpO2 values from training ratios, to estimate the SpO2 values corresponding to the determined ratios.

Figure 8:
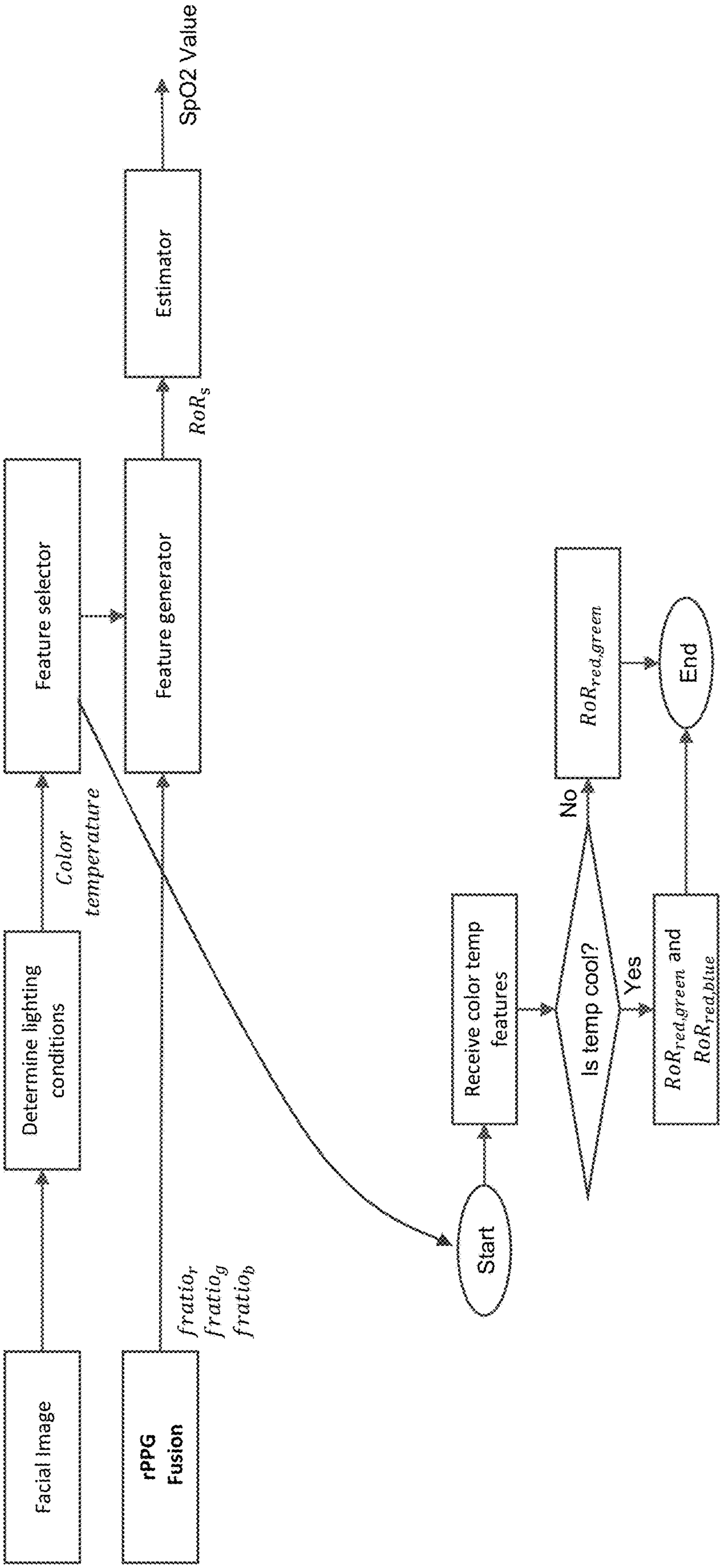
FIG. 8 illustrates an example process for selecting color channels based on lighting conditions.

FIG. 8 illustrates an example process for selecting color channels based on lighting conditions to compensate for the effects of wide-band light spectrum. In the example of FIG. 8, the sequence of images (e.g., facial images) are used to determine the lighting conditions in those images. The lighting conditions can include lighting properties such as color temperature, i.e., classified as warm, neutral, or cool. For example, the color temperature can be estimated by a deep learning model trained on facial images, with various skin tones, under different brightness, and the ground-truth annotations on color temperature. As another example, for facial images, a person's eyes and teeth can be used to estimate the color temperature. As another example, a display showing a neutral color board can be used to estimate the color temperature.

The lighting conditions are provided to a feature selector block, which selects the color-pairs to use for SpO2 estimation. For example, in FIG. 8, the feature selector receives features regarding the color temperature. If the color temperature is not cool, then red and green are selected as the color channels to use for providing an SpO2 estimation. However, if the temperature is cool, then light intensity will be weaker in the red band, and both red,green and red,blue ratios are selected. In the example of FIG. 8, the feature generator takes the color channels determined by the feature selector and generates the RoR(s) for the determined color pairs. The feature generator generates the RoR(s) by dividing the fused ROI ratio values for the respective colors. In the example of FIG. 8, the estimator receives the RoR(s) and generates SpO2 estimation values, e.g., using a machine learning model. In one embodiment, a SVR with nonlinear RBF kernel is used to establish a regression model according to $f:\{RoR_{Red,\ Green}, RoR_{Red,\ Blue}\} \rightarrow SpO_2$ Particular embodiments may store the resulting SpO2 estimates for the user. Particular embodiments may display SpO2 estimates in real-time or near real-time e.g., in a health application on a user's computing device. Particular embodiments may provide these estimates to a health provider, e.g., the person's doctor. Particular embodiments may create an alert or alarm, e.g., to the user or to medical personnel, when the user's SpO2 level is determined to be below a threshold level.

Particular embodiments may repeat one or more steps of the method of FIG. 3, where appropriate. Although this disclosure describes and illustrates particular steps of the method of FIG. 3 as occurring in a particular order, this disclosure contemplates any suitable steps of the method of FIG. 3 occurring in any suitable order. Moreover, although this disclosure describes and illustrates particular components, devices, or systems carrying out particular steps of the method of FIG. 3, such as the computer system of FIG. 10, this disclosure contemplates any suitable combination of any suitable components, devices, or systems carrying out any suitable steps of the method of FIG. 3. Moreover, this disclosure contemplates that some or all of the computing operations described herein, including the steps of the example method illustrated in FIG. 3, may be performed by circuitry of a computing device, for example the computing device of FIG. 10, by a processor coupled to non-transitory computer readable storage media, or any suitable combination thereof.

Ambient light that has a relatively stronger light intensity in longer wavelengths, which corresponds to a lower color temperature, provides relatively better discrimination power between oxygenated and deoxygenated hemoglobin, thereby providing relatively better SpO2 estimates using remote PPG. Particular embodiments may use one or more display screens in the person's environment to generate pure selected colors (e.g., pure red, pure green, etc.). For example, a display of a user's smartphone or TV may be instructed to generate a pure red image, creating red illumination, while images of the person's skin are being captured. Particular embodiments may train an SpO2 estimation model using these same light source(s). Particular embodiments may determine the distance between the user's face and the display, and use this information when making SpO2 estimates.

The color channels on a consumer RGB camera can have a relatively low color selectivity, i.e., other color components can leak into a specific channel. For example, the photons sensed by a consumer camera in the green channel include photons in neighboring blue and red channels, not just photons corresponding to the green channel. This color leaking reduces the linearity of the discrimination power between oxygenated and deoxygenated hemoglobin, complicating SpO2 estimation. Therefore, particular embodiments synchronize lighting source(s) and a camera's shutter (e.g., a smartphone camera shutter), such that the shutter is open while a red color is displayed on the display, then closes, then re-opens when a green color is displayed on the display, etc. Particular embodiments may cycle through an, e.g., red-green-blue display/shutter sequence n number of times to capture a sequence of images. Particular embodiments may assign images frames to R, G, or B corresponding to the point in the red-blue-green sequence in which those images were taken. In the rPPG extraction and processing steps (e.g., the rPPG buffering and extraction process of FIG. 5), the red rPPG signals $$rPPG_r^{ROI\ i}$$

are extracted from red color channel from the red portion of the sequence; the green rPPG signals $$rPPG_g^{ROI\ i}$$

are extracted from green color channel from the green portion of the sequence; and the blue rPPG signals $$rPPG_b^{ROI\ i}$$

are extracted from blue color channel from the blue portion of the sequence. Particular embodiments may use an IR light (e.g., from an IR LED emitter) to illuminate a person's skin, and similar to the process above, may also synchronize the camera shutter with activation of the IR light. For example, one image frame may involve opening the shutter while red light is displayed on, e.g., a smartphone screen, while another image frame may involve opening the shutter while the display screen is off and an IR LED light on the smartphone illuminates the user.

Figure 9:
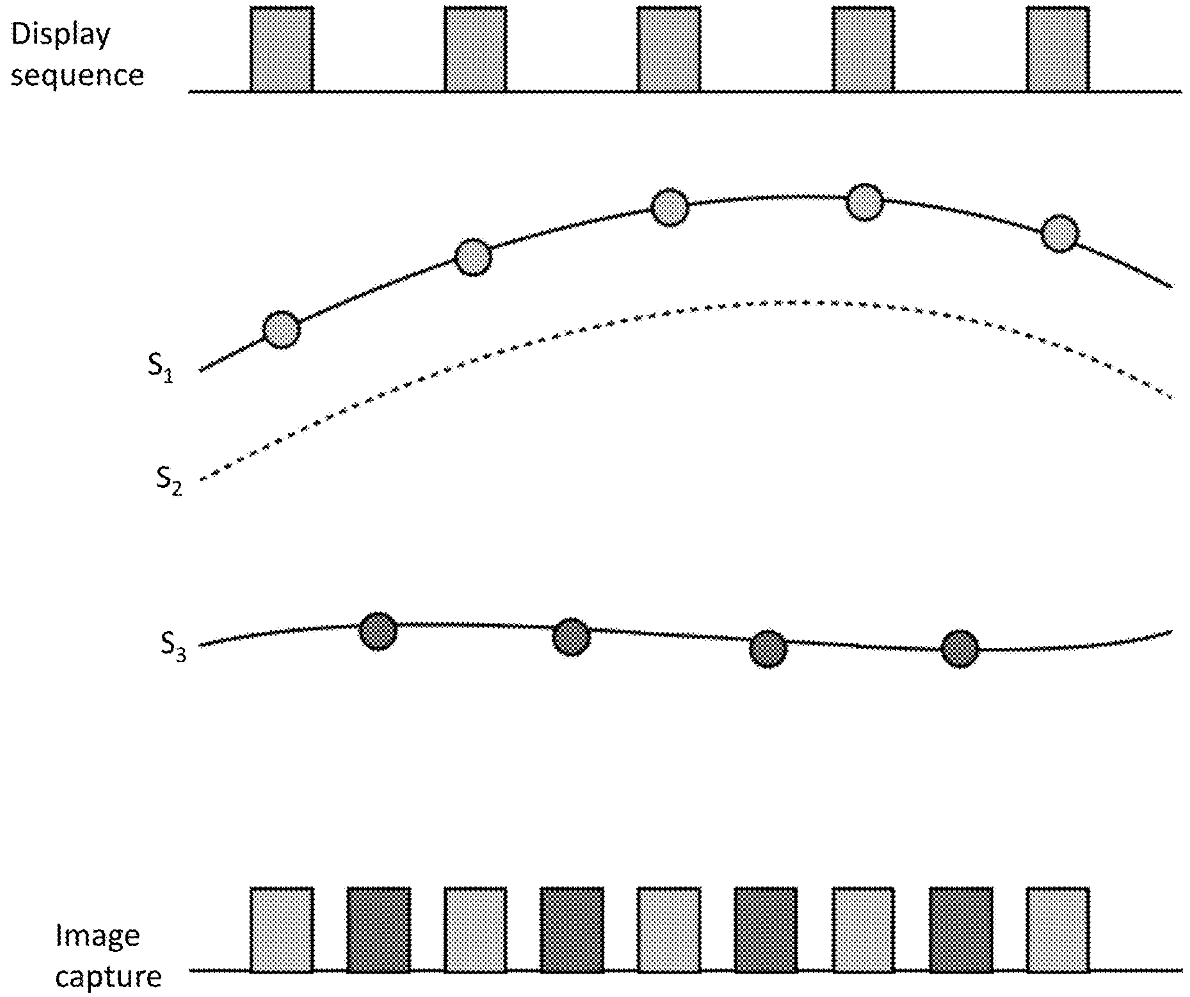
FIG. 9 illustrates an example of subtracting non-enhanced ambient light from a sequence of images to create an enhanced rPPG signal.

Particular embodiments may remove the presence of non-controlled ambient light in a sequence of images. For example, particular embodiments may use a display screen, such as a smartphone or TV screen, to create enhanced light as described above. A camera may take an alternating sequence of images of a person under this enhanced light and without this enhanced light. The non-enhanced ambient light can then be extracted from the image sequence, and SpO2 can be determined using only the enhanced-light images. FIG. 9 illustrates an example of subtracting non-enhanced ambient light from a sequence of images to create an enhanced rPPG signal $S_2$. As illustrated in FIG. 9, a display or emitter alternates between displaying an image (e.g., a red color, IR light, a green color, etc.) and turning off. A camera operating at, e.g., 60 frames per second, captures images while the display is on and while the display is off. The images are used to generate an rPPG signal $S_1$ corresponding to images when the display is on and an rPPG signal $S_3$ corresponding to when the display is off. The enhanced signal $S_2$ can then be determined by subtracting $S_3$ from $S_1$.

Particular embodiments may capture a sequence of images and perform SpO2 estimates periodically (e.g., every 30 seconds, every 1 minute, every hour, etc.), for example on a schedule set by a user. Particular embodiments may perform SpO2 estimates on demand. Particular embodiments may perform SpO2 estimates passively, e.g., while a user is viewing content on their smartphone or TV or otherwise occupying an ambiently-lit space (e.g., while exercising, reading, etc.). Particular embodiments may include providing enhanced lighting conditions, such as from a device display, in order to provide better detection accuracy. Particular embodiments may capture a sequence of images while instructing a user to remain still, e.g., by keeping their face in a box displayed on a display.

Figure 10:
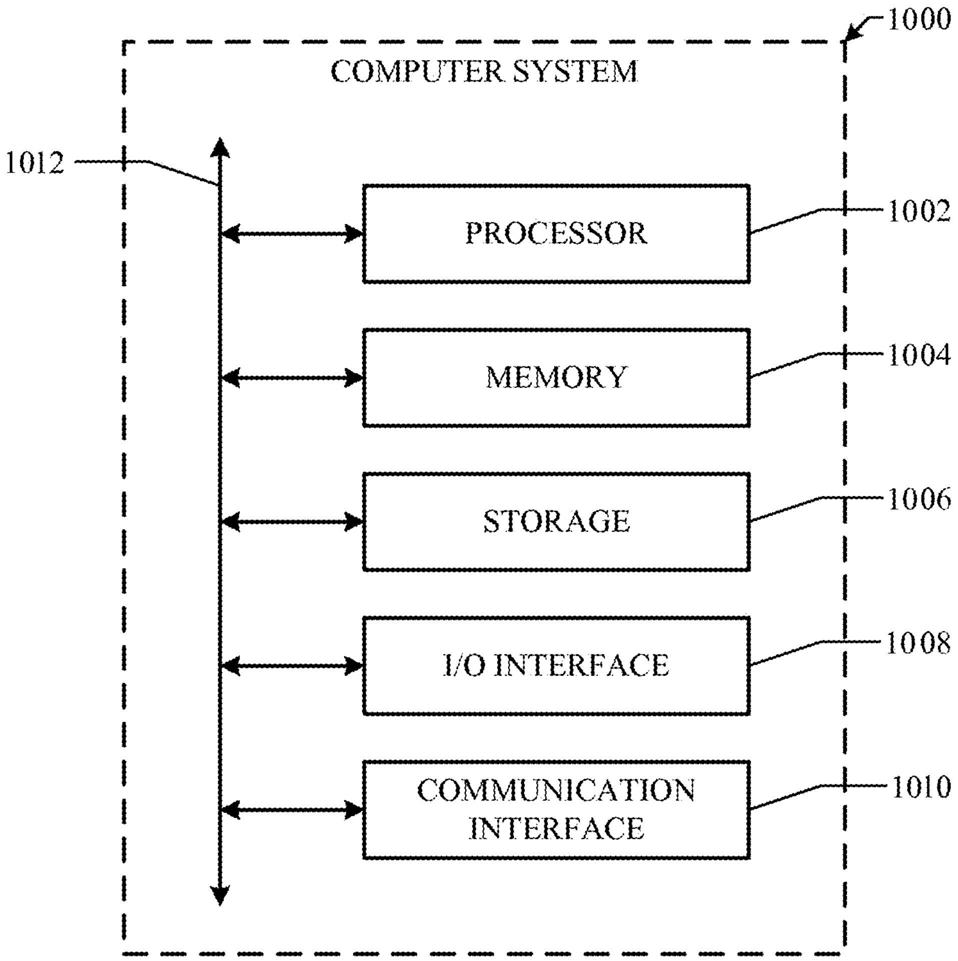
FIG. 10 illustrates an example computing system.

FIG. 10 illustrates an example computer system 1000. In particular embodiments, one or more computer systems 1000 perform one or more steps of one or more methods described or illustrated herein. In particular embodiments, one or more computer systems 1000 provide functionality described or illustrated herein. In particular embodiments, software running on one or more computer systems 1000 performs one or more steps of one or more methods described or illustrated herein or provides functionality described or illustrated herein. Particular embodiments include one or more portions of one or more computer systems 1000. Herein, reference to a computer system may encompass a computing device, and vice versa, where appropriate. Moreover, reference to a computer system may encompass one or more computer systems, where appropriate.

This disclosure contemplates any suitable number of computer systems 1000. This disclosure contemplates computer system 1000 taking any suitable physical form. As example and not by way of limitation, computer system 1000 may be an embedded computer system, a system-on-chip (SOC), a single-board computer system (SBC) (such as, for example, a computer-on-module (COM) or system-on-module (SOM)), a desktop computer system, a laptop or notebook computer system, an interactive kiosk, a mainframe, a mesh of computer systems, a mobile telephone, a personal digital assistant (PDA), a server, a tablet computer system, or a combination of two or more of these. Where appropriate, computer system 1000 may include one or more computer systems 1000; be unitary or distributed; span multiple locations; span multiple machines; span multiple data centers; or reside in a cloud, which may include one or more cloud components in one or more networks. Where appropriate, one or more computer systems 1000 may perform without substantial spatial or temporal limitation one or more steps of one or more methods described or illustrated herein. As an example and not by way of limitation, one or more computer systems 1000 may perform in real time or in batch mode one or more steps of one or more methods described or illustrated herein. One or more computer systems 1000 may perform at different times or at different locations one or more steps of one or more methods described or illustrated herein, where appropriate.

In particular embodiments, computer system 1000 includes a processor 1002, memory 1004, storage 1006, an input/output (I/O) interface 1008, a communication interface 1010, and a bus 1012. Although this disclosure describes and illustrates a particular computer system having a particular number of particular components in a particular arrangement, this disclosure contemplates any suitable computer system having any suitable number of any suitable components in any suitable arrangement.

In particular embodiments, processor 1002 includes hardware for executing instructions, such as those making up a computer program. As an example and not by way of limitation, to execute instructions, processor 1002 may retrieve (or fetch) the instructions from an internal register, an internal cache, memory 1004, or storage 1006; decode and execute them; and then write one or more results to an internal register, an internal cache, memory 1004, or storage 1006. In particular embodiments, processor 1002 may include one or more internal caches for data, instructions, or addresses. This disclosure contemplates processor 1002 including any suitable number of any suitable internal caches, where appropriate. As an example and not by way of limitation, processor 1002 may include one or more instruction caches, one or more data caches, and one or more translation lookaside buffers (TLBs). Instructions in the instruction caches may be copies of instructions in memory 1004 or storage 1006, and the instruction caches may speed up retrieval of those instructions by processor 1002. Data in the data caches may be copies of data in memory 1004 or storage 1006 for instructions executing at processor 1002 to operate on; the results of previous instructions executed at processor 1002 for access by subsequent instructions executing at processor 1002 or for writing to memory 1004 or storage 1006; or other suitable data. The data caches may speed up read or write operations by processor 1002. The TLBs may speed up virtual-address translation for processor 1002. In particular embodiments, processor 1002 may include one or more internal registers for data, instructions, or addresses. This disclosure contemplates processor 1002 including any suitable number of any suitable internal registers, where appropriate. Where appropriate, processor 1002 may include one or more arithmetic logic units (ALUs); be a multi-core processor; or include one or more processors 1002. Although this disclosure describes and illustrates a particular processor, this disclosure contemplates any suitable processor.

In particular embodiments, memory 1004 includes main memory for storing instructions for processor 1002 to execute or data for processor 1002 to operate on. As an example and not by way of limitation, computer system 1000 may load instructions from storage 1006 or another source (such as, for example, another computer system 1000) to memory 1004. Processor 1002 may then load the instructions from memory 1004 to an internal register or internal cache. To execute the instructions, processor 1002 may retrieve the instructions from the internal register or internal cache and decode them. During or after execution of the instructions, processor 1002 may write one or more results (which may be intermediate or final results) to the internal register or internal cache. Processor 1002 may then write one or more of those results to memory 1004. In particular embodiments, processor 1002 executes only instructions in one or more internal registers or internal caches or in memory 1004 (as opposed to storage 1006 or elsewhere) and operates only on data in one or more internal registers or internal caches or in memory 1004 (as opposed to storage 1006 or elsewhere). One or more memory buses (which may each include an address bus and a data bus) may couple processor 1002 to memory 1004. Bus 1012 may include one or more memory buses, as described below. In particular embodiments, one or more memory management units (MMUs) reside between processor 1002 and memory 1004 and facilitate accesses to memory 1004 requested by processor 1002. In particular embodiments, memory 1004 includes random access memory (RAM). This RAM may be volatile memory, where appropriate Where appropriate, this RAM may be dynamic RAM (DRAM) or static RAM (SRAM). Moreover, where appropriate, this RAM may be single-ported or multi-ported RAM. This disclosure contemplates any suitable RAM. Memory 1004 may include one or more memories 1004, where appropriate. Although this disclosure describes and illustrates particular memory, this disclosure contemplates any suitable memory.

In particular embodiments, storage 1006 includes mass storage for data or instructions. As an example and not by way of limitation, storage 1006 may include a hard disk drive (HDD), a floppy disk drive, flash memory, an optical disc, a magneto-optical disc, magnetic tape, or a Universal Serial Bus (USB) drive or a combination of two or more of these. Storage 1006 may include removable or non-removable (or fixed) media, where appropriate. Storage 1006 may be internal or external to computer system 1000, where appropriate. In particular embodiments, storage 1006 is non-volatile, solid-state memory. In particular embodiments, storage 1006 includes read-only memory (ROM). Where appropriate, this ROM may be mask-programmed ROM, programmable ROM (PROM), erasable PROM (EPROM), electrically erasable PROM (EEPROM), electrically alterable ROM (EAROM), or flash memory or a combination of two or more of these. This disclosure contemplates mass storage 1006 taking any suitable physical form. Storage 1006 may include one or more storage control units facilitating communication between processor 1002 and storage 1006, where appropriate. Where appropriate, storage 1006 may include one or more storages 1006. Although this disclosure describes and illustrates particular storage, this disclosure contemplates any suitable storage.

In particular embodiments, I/O interface 1008 includes hardware, software, or both, providing one or more interfaces for communication between computer system 1000 and one or more I/O devices. Computer system 1000 may include one or more of these I/O devices, where appropriate. One or more of these I/O devices may enable communication between a person and computer system 1000. As an example and not by way of limitation, an I/O device may include a keyboard, keypad, microphone, monitor, mouse, printer, scanner, speaker, still camera, stylus, tablet, touch screen, trackball, video camera, another suitable I/O device or a combination of two or more of these. An I/O device may include one or more sensors. This disclosure contemplates any suitable I/O devices and any suitable I/O interfaces 1008 for them. Where appropriate, I/O interface 1008 may include one or more device or software drivers enabling processor 1002 to drive one or more of these I/O devices. I/O interface 1008 may include one or more I/O interfaces 1008, where appropriate. Although this disclosure describes and illustrates a particular I/O interface, this disclosure contemplates any suitable I/O interface.

In particular embodiments, communication interface 1010 includes hardware, software, or both providing one or more interfaces for communication (such as, for example, packet-based communication) between computer system 1000 and one or more other computer systems 1000 or one or more networks. As an example and not by way of limitation, communication interface 1010 may include a network interface controller (NIC) or network adapter for communicating with an Ethernet or other wire-based network or a wireless NIC (WNIC) or wireless adapter for communicating with a wireless network, such as a WI-FI network. This disclosure contemplates any suitable network and any suitable communication interface 1010 for it. As an example and not by way of limitation, computer system 1000 may communicate with an ad hoc network, a personal area network (PAN), a local area network (LAN), a wide area network (WAN), a metropolitan area network (MAN), or one or more portions of the Internet or a combination of two or more of these. One or more portions of one or more of these networks may be wired or wireless. As an example, computer system 1000 may communicate with a wireless PAN (WPAN) (such as, for example, a BLUETOOTH WPAN), a WI-FI network, a WI-MAX network, a cellular telephone network (such as, for example, a Global System for Mobile Communications (GSM) network), or other suitable wireless network or a combination of two or more of these. Computer system 1000 may include any suitable communication interface 1010 for any of these networks, where appropriate. Communication interface 1010 may include one or more communication interfaces 1010, where appropriate. Although this disclosure describes and illustrates a particular communication interface, this disclosure contemplates any suitable communication interface.

In particular embodiments, bus 1012 includes hardware, software, or both coupling components of computer system 1000 to each other. As an example and not by way of limitation, bus 1012 may include an Accelerated Graphics Port (AGP) or other graphics bus, an Enhanced Industry Standard Architecture (EISA) bus, a front-side bus (FSB), a HYPERTRANSPORT (HT) interconnect, an Industry Standard Architecture (ISA) bus, an INFINIBAND interconnect, a low-pin-count (LPC) bus, a memory bus, a Micro Channel Architecture (MCA) bus, a Peripheral Component Interconnect (PCI) bus, a PCI-Express (PCIe) bus, a serial advanced technology attachment (SATA) bus, a Video Electronics Standards Association local (VLB) bus, or another suitable bus or a combination of two or more of these. Bus 1012 may include one or more buses 1012, where appropriate. Although this disclosure describes and illustrates a particular bus, this disclosure contemplates any suitable bus or interconnect.

Herein, a computer-readable non-transitory storage medium or media may include one or more semiconductor-based or other integrated circuits (ICs) (such, as for example, field-programmable gate arrays (FPGAs) or application-specific ICs (ASICs)), hard disk drives (HDDs), hybrid hard drives (HHDs), optical discs, optical disc drives (ODDs), magneto-optical discs, magneto-optical drives, floppy diskettes, floppy disk drives (FDDs), magnetic tapes, solid-state drives (SSDs), RAM-drives, SECURE DIGITAL cards or drives, any other suitable computer-readable non-transitory storage media, or any suitable combination of two or more of these, where appropriate. A computer-readable non-transitory storage medium may be volatile, non-volatile, or a combination of volatile and non-volatile, where appropriate.

Herein, "or" is inclusive and not exclusive, unless expressly indicated otherwise or indicated otherwise by context. Therefore, herein, "A or B" means "A, B, or both," unless expressly indicated otherwise or indicated otherwise by context. Moreover, "and" is both joint and several, unless expressly indicated otherwise or indicated otherwise by context. Therefore, herein, "A and B" means "A and B, jointly or severally," unless expressly indicated otherwise or indicated otherwise by context.

The scope of this disclosure encompasses all changes, substitutions, variations, alterations, and modifications to the example embodiments described or illustrated herein that a person having ordinary skill in the art would comprehend. The scope of this disclosure is not limited to the example embodiments described or illustrated herein. Moreover, although this disclosure describes and illustrates respective embodiments herein as including particular components, elements, feature, functions, operations, or steps, any of these embodiments may include any combination or permutation of any of the components, elements, features, functions, operations, or steps described or illustrated anywhere herein that a person having ordinary skill in the art would comprehend.

What is claimed is:

1. A method comprising:

accessing a sequence of images of a portion of a person's skin illuminated by ambient light;

determining, from at least one of the images, a plurality of microregions in the portion of the person's skin;

determining, based on a similarity between particular microregions of the plurality of microregions, one or more regions of interest of the person's skin by combining a first particular microregion and a second particular microregion into a region of interest based on one or more of (1) an amount of similarity between a skin property of the first particular microregion and a skin property of the second particular microregion or (2) an amount of spatial symmetry between the first particular microregion and the second particular microregion;

determining, for each of the one or more regions of interest, a remote photoplethysmogram (rPPG) signal based on the sequence of images; and determining, based on one or more of the rPPG signals from the determined one or more regions of interest, an estimate of an oxygen saturation in the person's blood.

2. The method of claim 1, wherein the portion of the person's skin comprises the person's face.

3. The method of claim 1, wherein the skin property comprises a plurality of skin properties.

4. The method of claim 1, wherein the skin property comprises an average intensity, for each of one or more color channels, of pixels within that microregion.

5. The method of claim 4, wherein determining, based on a similarity between particular microregions of the plurality of microregions, one or more regions of interest of the person's skin comprises:

determining, for a first pair of particular microregions, a difference between the skin properties of the first pair of particular microregions;

comparing the determined difference in skin properties to a first threshold; and in response to a determination that the determined difference is less than the first threshold, then combining the first pair of particular microregions into a region of interest.

6. The method of claim 5, further comprising:

determining, for a second pair of particular microregions, a difference between the skin properties of the second pair of particular microregions in response to a determination that the determined difference for the second pair of particular microregions is not less than first threshold, then:

comparing the determined difference to a second threshold;

in response to a determination that the determined difference is less than the second threshold, then determining whether the second pair of particular microregions exhibit a spatial symmetry; and in response to a determination that the pair of particular microregions exhibit a spatial symmetry, then combining the second pair of particular microregions into a region of interest.

7. The method of claim 5, wherein a value of the first threshold is based at least in part on one or more of:

a skin tone of the person;

an intensity of the ambient light; or a spatially varying distribution of the intensity of the ambient light.

8. The method of claim 1, further comprising calculating, for each region of interest, a plurality of first ratios, each first ratio corresponding to a particular color channel.

9. The method of claim 1, wherein determining, based on one or more of the rPPG signals, an estimate of an oxygen saturation in the person's blood further comprises estimating the oxygen saturation based on a weighted combination of each rPPG signal, wherein each weight is determined according to a corresponding pulse transit time.

10. The method of claim 1, further comprising estimating the oxygen saturation based on a ratio-of-ratios of a pair of color channels, wherein the pair of color channels is determined based on a color temperature of the ambient lighting.

11. The method of claim 1, wherein the ambient light comprises light from a display screen of an electronic device.

12. The method of claim 11, wherein the light from the display screen consists of a particular color corresponding to one of a plurality of color channels.

13. One or more non-transitory computer readable storage media storing instructions and coupled to one or more processors that are operable to execute the instructions to:

access a sequence of images of a portion of a person's skin illuminated by ambient light;

determine, from at least one of the images, a plurality of microregions in the portion of the person's skin;

determine, based on a similarity between particular microregions of the plurality of microregions, one or more regions of interest of the person's skin by combining a first particular microregion and a second particular microregion into a region of interest based on one or more of (1) an amount of similarity between a skin property of the first particular microregion and a skin property of the second particular microregion or (2) an amount of spatial symmetry between the first particular microregion and the second particular microregion;

determine, for each of the one or more regions of interest, a remote photoplethysmogram (rPPG) signal based on the sequence of images; and determine based on one or more of the rPPG signals from the determined one or more regions of interest, an estimate of an oxygen saturation in the person's blood.

14. The media of claim 13, wherein the portion of the person's skin comprises the person's face.

15. The media of claim 13, wherein the skin property comprises a plurality of skin properties.

16. The media of claim 13, wherein the skin property comprises an average intensity, for each of one or more color channels, of pixels within that microregion.

17. A system comprising:

one or more non-transitory computer readable storage media storing instructions; and one or more processors coupled to the non-transitory computer readable storage media, the one or more processors operable to execute the instructions to:

access a sequence of images of a portion of a person's skin illuminated by ambient light;

determine, from at least one of the images, a plurality of microregions in the portion of the person's skin;

determine, based on a similarity between particular microregions of the plurality of microregions, one or more regions of interest of the person's skin by combining a first particular microregion and a second particular microregion into a region of interest based on one or more of (1) an amount of similarity between a skin property of the first particular microregion and a skin property of the second particular microregion or (2) an amount of spatial symmetry between the first particular microregion and the second particular microregion;

determine, for each of the one or more regions of interest, a remote photoplethysmogram (rPPG) signal based on the sequence of images; and determine based on one or more of the rPPG signals from the determined one or more regions of interest, an estimate of an oxygen saturation in the person's blood.

18. The system of claim 17, wherein the portion of the person's skin comprises the person's face.

19. The system of claim 17, wherein the skin property comprises a plurality of skin properties.

20. The system of claim 17, wherein the skin property comprises an average intensity, for each of one or more color channels, of pixels within that microregion.

* * * * *